US00PP34498P2

(12) United States Plant Patent
Yamada et al.

(10) Patent No.: US PP34,498 P2
(45) Date of Patent: Aug. 16, 2022

(54) ***MANDEVILLA* PLANT NAMED 'SUNPA 6173'**

(50) Latin Name: *Mandevilla hybrida*
Varietal Denomination: Sunpa 6173

(71) Applicants: Masahiro Yamada, Shiga (JP); Tomoya Misato, Shiga (JP)

(72) Inventors: Masahiro Yamada, Shiga (JP); Tomoya Misato, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 17/571,474

(22) Filed: Jan. 8, 2022

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Annette H Para
(74) *Attorney, Agent, or Firm* — C. Anne Whealy

(57) ABSTRACT

A new and distinct cultivar of *Mandevilla* plant named 'Sunpa 6173', characterized by its upright plant habit; vigorous growth habit; freely branching habit; early and freely flowering habit; long flowering period; and medium-sized red-colored flowers with orangish yellow-colored centers.

1 Drawing Sheet

Figure 1:
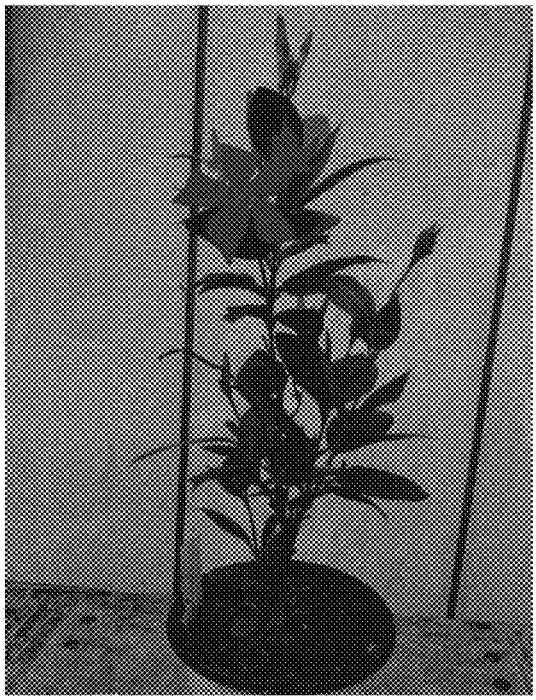

Botanical designation: *Mandevilla hybrida.*
Cultivar denomination: 'SUNPA 6173'.

STATEMENT REGARDING PRIOR DISCLOSURES BY THE INVENTORS/APPLICANTS & ASSIGNEE

The Inventors/Applicants and Assignee assert that no publications nor advertisements relating to sales, offers for sale or public distribution occurred more than one year prior to the effective filing date of this application. Any information about the claimed plant would have been obtained from a direct or indirect disclosure from the Inventors/Applicants and/or Assignee. Inventors/Applicants and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla hybrida* and hereinafter referred to by the name 'Sunpa 6173'.

The new *Mandevilla* plant is a product of a planned breeding program conducted by the Inventors in Higashiomi, Shiga, Japan. The objective of the breeding program is to create new upright and freely branching *Mandevilla* plants with freely flowering habit and attractive flowers.

The new *Mandevilla* plant originated from a cross-pollination conducted by the Inventors in Higashiomi, Shiga, Japan in October, 2014 of a proprietary selection of *Mandevilla hybrida* identified as code number 13M-41-7, not patented, as the female, or seed parent with a proprietary selection of *Mandevilla hybrida* identified as code number M37-1, not patented, as the male, or pollen, parent. The new *Mandevilla* plant was discovered and selected by the Inventors as a single flowering plant from within the progeny of the stated cross-pollination in a controlled greenhouse environment in Higashiomi, Shiga, Japan in September, 2016.

Asexual reproduction of the new *Mandevilla* plant by terminal vegetative cuttings in Higashiomi, Shiga, Japan since March, 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 6173'. These characteristics in combination distinguish 'Sunpa 6173' as a new and distinct *Mandevilla* plant:

1. Upright plant habit.
2. Vigorous growth habit.
3. Freely branching habit.
4. Early and freely flowering habit.
5. Long flowering period.
6. Medium-sized red-colored flowers with orangish yellow-colored centers.

Plants of the new *Mandevilla* can be compared to plants of the female and male parent selections. Plants of the new *Mandevilla* differ primarily from plants of the parent selections in plant habit as plants of the new *Mandevilla* are upright whereas plants of the parent selections are semi-upright.

Plants of the new *Mandevilla* can be compared to plants of the *Mandevilla atroviolacea* X (*Mandevilla amabilis* x *M. boliviensis*) 'Sunmandecrim', disclosed in U.S. Plant Pat. No. 15,539. In side-by-side comparisons, plants of the new *Mandevilla* differ from plants of 'Sunmandecrim' in the following characteristics:

1. Plants of the new *Mandevilla* have shorter internodes than plants of 'Sunmandecrim'.
2. Leaves of plants of the new *Mandevilla* are decussate whereas leaves of plants of 'Sunmandecrim' are opposite.
3. Plants of the new *Mandevilla* flower earlier than plants of 'Sunmandecrim'.
4. Plants of the new *Mandevilla* have smaller flowers than plants of 'Sunmandecrim'.
5. Petals of plants of the new *Mandevilla* are not imbricate whereas petals of plants of 'Sunmandecrim' are imbricate.
6. Petals of plants of the new *Mandevilla* are lighter red in color than petals of plants of 'Sunmandecrim'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet (FIG. 1) is a side perspective view of a typical flowering plant of 'Sunpa 6173' grown in a container.

Figure 2:
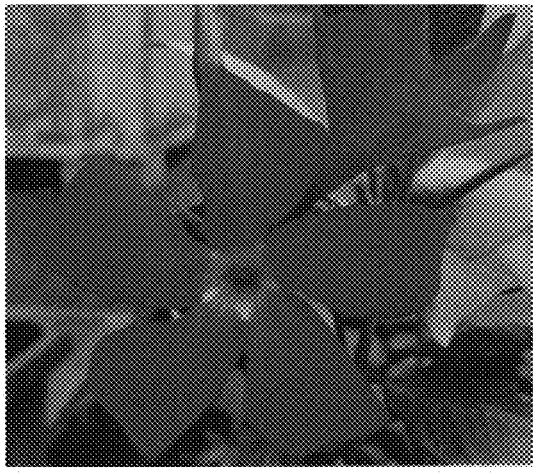

The photograph at the bottom of the sheet (FIG. 2) is a close-up view of a typical flower of 'Sunpa 6173'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 6173'.

Parentage:

*Female, or seed, parent*.—Proprietary selection of *Mandevilla hybrida* identified as code number 13M-41-7, not patented.

*Male, or pollen, parent*.—Proprietary selection of *Mandevilla hybrida* identified as code number M37-1, not patented.

Propagation:

*Type*.—By terminal vegetative cuttings.

*Time to initiate roots, summer and winter*.—About two weeks at temperatures about 23° C. to 25° C.

*Time to produce a rooted young plant, summer and winter*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright plant habit; vigorous growth habit; freely branching habit; suitable for hanging baskets and garden plantings.

*Plant height*.—About 40 cm.

*Plant diameter*.—About 15 cm.

*Lateral branch description*.—Length: About 14.3 cm. Diameter: About 1.7 mm. Internode length: About 2 cm. Strength: Strong, flexible. Texture: Smooth, glabrous. Color, developing: Close to 144A. Color, fully developed: Close to 199A.

Leaf description:

*Arrangement and quantity*.—Decussate, simple; about five to eight per lateral branch.

*Length*.—About 5.9 cm.

*Width*.—About 3.1 cm.

*Shape*.—Elliptic.

*Apex*.—Acuminate.

*Base*.—Rounded.

*Margin*.—Entire; not undulate to slightly undulate.

*Texture and luster, upper and lower surfaces*.—Smooth, glabrous; slightly glossy.

*Venation pattern*.—Pinnate, reticulate.

*Color*.—Developing leaves, upper surface: Close to 146B. Developing leaves, lower surface: Close to 138A. Fully expanded leaves, upper surface: Close to 137B; venation, close to 138A. Fully expanded leaves, lower surface: Close to 199B; venation, close to 138B.

*Petioles*.—Length: About 5 mm. Diameter: About 1.9 mm. Texture, upper and lower surfaces: Smooth, glabrous. Color, upper and lower surfaces: Close to 138A.

Flower description:

*Flower type and habit*.—Single salverform flowers; flowers face mostly upright to outwardly; freely flowering habit with about three to five flowers per axil.

*Natural flowering season*.—Early flowering habit, plants begin flowering about six weeks after planting rooted cuttings; long flowering period, plants flower continuously from summer until late autumn in Japan.

*Flower longevity on the plant*.—About seven to ten days; flowers not persistent.

*Fragrance*.—None detected.

*Flower buds*.—Height: About 3.3 cm. Diameter: About 4.9 mm. Shape: Rhombic. Color: Proximally, close to 149B and distally, close to 50B.

*Flowers*.—Appearance: Salverform; flared trumpet, corolla fused and five-parted; flowers roughly star-shaped. Diameter: About 5.7 cm. Depth (length): About 3.4 cm. Throat diameter: About 8 mm. Tube length: About 1.1 cm. Tube diameter, proximally: About 3 mm.

*Corolla*.—Quantity and arrangement: Five petals arranged in a single whorl and fused towards the base into an elongated tube; petal lobes not imbricate. Petal lobe length: About 2.6 cm. Petal lobe width: About 1.7 cm. Petal lobe shape: Spatulate, asymmetrical. Petal lobe apex: Acuminate. Petal lobe margin: Entire; not undulate. Petal lobe texture and luster, upper and lower surfaces: Smooth, glabrous; velvety; matte. Throat texture: Smooth, glabrous; velvety. Tube texture: Smooth, glabrous; velvety. Color: Petal lobe, when opening, upper surface: Close to 157A heavily overlain with close to 61D. Petal lobe, when opening, lower surface: Close to N57B and N57D. Petal lobe, fully opened, upper surface: Brighter than 45B; venation, similar to lamina; color does not change with subsequent development. Petal lobe, fully opened, lower surface: Close to N57B and N58C; venation, similar to lamina; color does not change with subsequent development. Throat: Proximally, close to 17B and distally, close to 13. Tube: Proximally, close to 150C and distally, close to 58B and 150C; at the base, close to 60C and 145C.

*Calyx*.—Quantity and arrangement: Five sepals arranged in a single whorl, fused at the base; calyx, star-shaped. Sepal length: About 8.6 mm. Sepal width: About 2.4 mm. Sepal shape: Lanceolate. Sepal apex: Acute. Sepal margin: Entire. Sepal texture, upper and lower surfaces: Smooth, glabrous. Sepal color, upper and lower surfaces: Proximally, close to 142A and distally, close to 63A.

*Peduncles*.—Length: About 3.5 cm. Diameter: About 2.1 mm. Texture: Smooth, glabrous. Aspect: Mostly upright. Color: Close to 138A.

*Pedicels*.—Length: About 1.3 cm. Diameter: About 2.1 mm. Texture: Smooth, glabrous. Aspect: Upright to outwardly. Color: Close to 180B.

*Reproductive organs*.—Stamens: Quantity and arrangement: Typically five; filaments fused to corolla; anthers, connivent. Anther size: About 2 mm by 6.6 mm. Anther shape: Lanceolate. Anther color: Close to 13B. Pollen amount: None observed. Pistils: Quantity: Typically one. Pistil length: About 1.2 cm. Style color: Close to 142D. Stigma shape: Conical. Stigma color: Close to 145C. Ovary color: Close to 142B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 6173' as illustrated and described.

* * * * *